United States Patent
Bestebreurtje

(10) Patent No.: US 8,020,446 B2
(45) Date of Patent: Sep. 20, 2011

(54) METHOD AND APPARATUS FOR DETECTING FLAWS IN A RAILHEAD

(75) Inventor: Pieter Bestebreurtje, Tiel (NL)

(73) Assignee: Sonimex B.V., Tiel (NL)

( * ) Notice: Subject to any disclaimer, the term of this patent is extended or adjusted under 35 U.S.C. 154(b) by 840 days.

(21) Appl. No.: 11/884,596

(22) PCT Filed: Jan. 12, 2006

(86) PCT No.: PCT/NL2006/000016
§ 371 (c)(1),
(2), (4) Date: Apr. 2, 2008

(87) PCT Pub. No.: WO2006/088353
PCT Pub. Date: Aug. 24, 2006

(65) Prior Publication Data
US 2008/0223137 A1     Sep. 18, 2008

(30) Foreign Application Priority Data
Feb. 17, 2005   (NL) ..................................... 1028325

(51) Int. Cl.
*G01N 29/04* (2006.01)
*G01N 29/00* (2006.01)
(52) U.S. Cl. ................ 73/628; 73/627; 73/636
(58) Field of Classification Search .............. 73/628, 73/624, 625, 634, 636, 639, 641, 866.5
See application file for complete search history.

(56) References Cited

U.S. PATENT DOCUMENTS

| | | | |
|---|---|---|---|
| 3,215,220 A | 11/1965 | Schoeffler | |
| 4,174,636 A | 11/1979 | Pagano et al. | |
| 4,700,574 A | 10/1987 | Turbe et al. | |
| 5,419,196 A * | 5/1995 | Havira et al. | 73/636 |
| 5,578,758 A | 11/1996 | Havira et al. | |
| 5,777,891 A | 7/1998 | Pagano et al. | |

(Continued)

FOREIGN PATENT DOCUMENTS

| | | |
|---|---|---|
| RU | 2 060 493 C1 | 5/1996 |
| RU | 2 184 960 C1 | 7/2002 |
| WO | WO 82/03920 | 11/1982 |

*Primary Examiner* — J M Saint Surin
(74) *Attorney, Agent, or Firm* — Weingarten, Schurgin, Gagnebin & Lebovici LLP

(57) ABSTRACT

A method for detecting flaws in a railhead, which railhead (1) is provided with a top side (T), a bottom side (B) and longitudinal sides (S) extending between that top side (T) and bottom side (B), wherein at least one ultrasonic first signal (10) is transmitted into the railhead (1) via said head top side (T) and traverses such a transmission path (9) that: —the signal (10) is only once reflected by the railhead bottom side (B), and not by a railhead longitudinal side (S); —the signal (10) reaches at least one substantially central railhead part (C); and —the signal (10) can exit the railhead (1) via the head top side (T); wherein first ultrasonic signals exiting the head top side (T) are detected, wherein the transmission path (9) of the at least first signal (10) extends in a virtual transmission plane, which transmission plane extends substantially transverse to a longitudinal direction (L) of the rail. In addition, the invention provides an apparatus for detecting flaws in a railhead. The invention further relates to a positioning method.

44 Claims, 8 Drawing Sheets

U.S. PATENT DOCUMENTS

| | | | |
|---|---|---|---|
| 5,804,731 A * | 9/1998 | Jaeggi | 73/636 |
| 6,347,550 B1 * | 2/2002 | Kroening et al. | 73/598 |
| 6,516,668 B2 * | 2/2003 | Havira et al. | 73/636 |
| 6,600,999 B2 * | 7/2003 | Clark et al. | 702/35 |
| 7,521,917 B2 * | 4/2009 | Katragadda et al. | 324/126 |
| 7,726,191 B2 * | 6/2010 | Bestebreurtje | 73/614 |

\* cited by examiner

METHOD AND APPARATUS FOR DETECTING FLAWS IN A RAILHEAD

This application is a §371 national phase filing of PCT/NL2006/000016 filed Jan. 12, 2006, and claims priority to Dutch application No. 1028325 filed Feb. 17, 2005.

One aspect of the invention relates to a method for detecting flaws in a railhead, which railhead is provided with a top side and a bottom side, and longitudinal sides extending between that top side and bottom side, wherein at least one ultrasonic first signal is transmitted into the railhead via this head top side and traverses such a transmission path that:

the signal is only once reflected by the railhead bottom side, and not by an above-mentioned railhead longitudinal side;

the signal reaches at least one substantially central railhead part; and the signal can exit the railhead via the head top side;

wherein ultrasonic first signals exiting the head top side are detected.

Such a method, which particularly comprises a transmission-mode method, is known from WO82/03920. Thus, FIGS. 1-3 of this international publication show how ultrasonic radiation is transmitted into the railhead by transducers $75_{1c}$ and $75_{2c}$ and is received again outside the railhead after reflection in the railhead. Here, the radiation traverses a transmission path 40, which extends in a rail longitudinal direction.

Further, WO82/03920 describes that a first series of transducers may be provided, in a first wheel, to transmit ultrasonic energy in the railhead in parallel paths at a first angle, and second series of transducers which is, longitudinally measured, arranged along the rail at a distance from the first series, in a second wheel, to receive the energy.

An advantage of this method is that a railhead can be checked for flaws, for instance defects and/or cracks in a non-destructive manner.

A disadvantage of the known method is that the transmission paths are relatively long. As a result, the known method is relatively susceptible to interference. Thus, in many cases, it is not exactly known what causes a detected change or interference of the ultrasonic radiation transmitted into the rail, for instance what type of flaw has been detected by means of the radiation. Further, the known method is, in particular, not well suitable for detecting substantially vertical longitudinal flaws in the railhead.

In WO82/03920, it is proposed to detect vertical rail longitudinal flaws (referred to as "vertical split heads") by means of transducers which transmit ultrasonic radiation in a "Z path" through the railhead. It is an object of WO82/03920 to detect such flaws in virtually every vertical plane of the railhead. A drawback of such Z-shaped transmission paths is that they are also relatively long and therefore result in a measurement which is relatively susceptible to interference. In addition, when traversing a Z path, the radiation is reflected in the railhead several times, on the longitudinal sides and bottom side of the railhead, which can cause extra interference and signal scattering.

In addition, from American patent U.S. Pat. No. 3,215,220, it is known to detect transverse railhead flaws by utilizing shear waves. This method is particularly sensitive to surfaces damages of the railhead, and therefore not suitable to detect flaws just below the rail surface, in the railhead.

American patent U.S. Pat. No. 4,700,574 also relates to the detection of transverse flaws, with transducers being arranged centrally on the rail, and transmitting ultrasonic signals into the rail in a downward inclined manner, and in a longitudinal direction of the rail. Here, the angle between the longitudinal center plane of the rail and a horizontal projection of the beam is $\alpha_1 = 20°$, and while the angle between the vertical center plane of the rail and a vertical projection of the beam is $\alpha_2 = 70°$. This method utilizes echo-mode measurements. A drawback is that this method is not suitable either for detecting substantially vertical longitudinal flaws in the railhead.

The present invention contemplates an improvement of a method for detecting flaws in a railhead. In one aspect, the invention contemplates a method with which substantially vertical railhead longitudinal flaws can be detected relatively reliably.

To this end, the method according to the invention is characterized in that the transmission path of the at least first signal extends in a virtual transmission plane, which transmission plane extends substantially transverse to a longitudinal direction of the rail.

In this manner, the first ultrasonic signal mentioned does not traverse a Z path. Thus, the first signal needs to traverse only a relatively short distance through the railhead, while, in addition, the signal is only once reflected by a side of the railhead. It is found that, thus, a surprisingly reliable and accurate flaw detection can be obtained, with which, in particular, most substantially vertical railhead longitudinal flaws can be detected well. It is noted that, herein, the term 'vertical' can be understood as being vertical with respect to the railhead, or substantially at right angles with respect to the top side of the railhead. In addition, it will be clear to a skilled person that, in the present application, a term "reflection by a side" means the same as "reflection on a side".

Further, it is found that most vertical railhead longitudinal flaws are precisely in or near the central railhead part. Accordingly, according to the invention, a railhead is preferably checked for these relatively central, vertical rail longitudinal flaws, while detection of vertical longitudinal flaws located near both sides of the railhead (as intended with Z path detection) is of secondary importance.

Various steps of the invention can be carried out in various orders. Thus, at least one ultrasonic first signal can first be transmitted into the railhead via the head top side mentioned, in order to traverse an above-mentioned transmission path. The transmission path extends, for instance, substantially transverse to the railhead. Then, the first signal can be reflected by the railhead bottom side, after which the signal can reach at least the substantially central railhead part. If there is no vertical longitudinal flaw in the central railhead part, the first signal, at least a substantial part thereof, can exit the railhead again via the head top side, in order to be detected by suitable detection means, such as an ultrasonic transducer or another suitable detector. When there is a vertical longitudinal flaw in the central railhead part, transmission of the first signal may be interfered by that flaw. Such an interference may also be detected by the detection means mentioned, for instance in order to be stored in combination with an associated railhead position.

In a reverse order, a first signal may, for instance, be transmitted into the railhead via the head top side mentioned, in order to traverse an above-mentioned transmission path. Then, the signal can reach at least the substantially central railhead part, in order to then be reflected by the railhead bottom side, back to the railhead top side. In this manner, the central railhead part can also be examined well for vertical longitudinal flaws.

Further, different first signals may, for instance, be transmitted successively in opposite directions straight through the railhead, within the framework of the invention, in order to test the head for the vertical longitudinal flaws mentioned.

In one aspect of the invention, a method for detecting flaws in a railhead, which railhead is provided with a top side and bottom side, is characterized in that at least one ultrasonic longitudinal sound signal is first transmitted from the railhead top side to the central railhead part, in order to then be able to reach the railhead bottom side, while a transmission path of the longitudinal sound signal extends in a virtual transmission plane, which transmission plane extends substantially transverse to a longitudinal direction of the rail, while ultrasonic signals exiting the head top side are detected by at least one detector.

Detection of an ultrasonic signal exiting the railhead top side may then mean that a longitudinal flaw is present in the central part of the railhead. If a vertical longitudinal flaw is present in the central railhead part, the longitudinal sound signal mentioned may, for instance, be converted and/or reflected under the influence of that flaw, such that the converted and/or reflected signal can exit again via the rail top side mentioned, for instance near the central railhead part, and can be detected by a detector. In this manner, a reliable detection of railhead longitudinal flaws can be obtained as well. Further, longitudinal sound is found to be particularly suitable to traverse the central railhead part, from the railhead top side and in the transmission plane mentioned, at a suitable angle for the purpose of flaw detection, as opposed to transverse sound.

Here, it is noted that the term longitudinal in "longitudinal sound" is not directly related to the rail longitudinal direction, but to the mode of the sound. With longitudinal sound, the sound wave of the sound signal is a longitudinal wave; here, the signal propagates via vibrations which are longitudinal to the direction of movement of the wave. Another mode of sound is, for instance, the transverse mode, where the sound is formed by shear waves.

It is advantageous when the longitudinal sound signal mentioned is, for instance, reflected by the railhead bottom side mentioned such that the reflected signal part exits the railhead at a distance from the central rail part, for instance such that that signal is substantially not received by an above-mentioned detector. In that case, with the aid of the detector, a good distinction can be made between detection of a flaw, where a signal reflected or converted by the flaw to the detector is received, or no detection of a flaw, where substantially no signal is received by the detector.

In one aspect of the invention, a method for detecting flaws in a railhead, which railhead is provided with a top side, is characterized in that at least one ultrasonic longitudinal sound signal is transmitted into the railhead via this head top side, such that at least a part of the longitudinal sound signal can propagate through the railhead as a creep wave near the head top side, while at least creep wave parts which have been reflected back from the railhead and exit the head top side are detected.

It is found that, in this manner, transverse flaws, which are located near the rail top surface in the railhead, can be detected well. The creep wave can propagate in a direction which is substantially parallel to the rail longitudinal direction and which is substantially parallel to the head top side mentioned. In particular, this creep wave can automatically propagate parallel to the rail surface, and is found to be disturbed surprisingly little by, for instance, indentations or other damages of the rail surface. The creep wave propagates just below the rail surface. Therefore, the creep wave should not be confused with a surface wave, which is only present in the surface. In addition to the creep wave, here, other longitudinal sound signals can also be transmitted through the railhead, at various angles, for the purpose of detection of transverse flaws. For this, for instance, various sound sources can be used. In addition, a signal from one sound source may, for instance, diverge, in particular when the sound source comprises a transducer with a relatively small crystal. In that case, a part of the diverging sound can form the creep wave mentioned which propagates parallel to the railhead top side, while another part of the sound does move away from the railhead top side. The present method may, for instance, utilize one or more transducers, which, for instance, operate in a single mode and/or dual mode (i.e. transmission mode).

In addition, the invention provides an apparatus for detecting flaws in a railhead. Such an apparatus is known per se from WO82/03920. According to the invention, a reliable detection apparatus is provided in that the apparatus is evidently intended and arranged for carrying out a method according to the invention.

One aspect of the invention relates to an assembly provided with a rail and an apparatus for detecting flaws in a railhead of the rail, while the railhead is provided with a top side and a bottom side. According to the invention, it is advantageous when the apparatus is movable over the top side of the railhead, in a particular direction of movement which is parallel to a rail longitudinal direction, while at least one first sound source of the apparatus can operatively be brought into such a position that a first ultrasonic signal transmitted by the first sound source:

enters the railhead via the head top side;
is only once reflected by the railhead bottom side, and not by a longitudinal side of the railhead;
reach at least one substantially central railhead part; and
can exit the railhead via the head top side;
while at least one first detector of the apparatus is arranged to detect ultrasonic first signals exiting the head top side.

The first sound source and first detector mentioned may, for instance, each simply be arranged along a same virtual transverse plane of the direction of movement mentioned. Each sound source mentioned may, for instance, comprise an ultrasonic transducer, or an ultrasonic laser source or another suitable ultrasonic sound source. Each sound detector may also be designed in different manners, and comprise, for instance, a suitable transducer or another suitable ultrasonic sound detector.

The first ultrasonic sound source may, for instance, operatively be able to be brought in such a respective transmitting position that a respective transmitting direction extends substantially transverse to a rail longitudinal direction, and is directed slightly away from a central railhead part. The first detector may, for instance, operatively be able to be brought in such a respective receiving position that a respective receiving direction extends substantially transverse to a rail longitudinal direction, and is directed slightly towards the central railhead part.

Each above-mentioned sound source can operatively transmit first signals, which traverse relatively short transmission paths, while the first signals are only once reflected by a railhead side, namely the bottom side. Therefore, the apparatus is relatively insusceptible to interference, and, for instance, less susceptible to pollution of the outside of the rail. With the apparatus, in particular, the vertical longitudinal flaws of a railhead can be discovered well.

According to one aspect of the invention, an assembly is provided with a rail and an apparatus for detecting flaws in a railhead of the rail, for instance an above-mentioned assembly, while the railhead is provided with a top side and a bottom side, while the apparatus is movable over the top side of the railhead, in a particular direction of movement which is parallel to a rail longitudinal direction, while the apparatus is provided with at least one sound source which is designed to transmit ultrasonic longitudinal sound, while the apparatus is provided with at least one receiver which is at least designed to detect ultrasonic sound, while the longitudinal sound source and the detector can operatively be brought into such a respective transmitting position and receiving position that a respective transmitting direction and respective receiving direction each extend substantially transverse to a rail longitudinal direction, and are directed to a central railhead part.

The longitudinal sound source and detector may, for instance, be used independently, or in combination with the first sound source and first detector mentioned. Use of longitudinal ultrasonic sound, in substantially transverse directions with respect to a rail longitudinal direction, has above-mentioned advantages and can provide a reliable detection of vertical rail longitudinal flaws. The assembly may, for instance, be provided with one or more transducers, which, for instance, operate in single mode and/or dual mode.

According to one aspect of the invention, an assembly is provided with a rail and an apparatus for detecting flaws in a railhead of the rail, characterized in that the apparatus is provided with at least one sound source which is arranged for transmitting at least one ultrasonic longitudinal sound signal into the railhead via the head top side mentioned, such that at least a part of the longitudinal sound signal propagates through the railhead as a creep wave near the head top side.

In this manner, substantially vertical transverse flaws of the railhead, which extend substantially transverse to the rail longitudinal direction, appear to be able to be detected as well in a surprisingly reliable manner.

Further, the invention provides an apparatus which is characterized by the measures of claim 28. The apparatus according to the invention may be provided with relatively few sound sources and detectors, for instance transducers, and have a compact design, while the apparatus can accurately and reliably detect various types of railhead defects. In addition, in this manner, the apparatus can be designed with relatively small transducers.

Further, the invention relates to a method for positioning an apparatus with respect to a rail. Such a method is described in WO82/03920, on p. 7, last paragraph, and comprises transmitting signals through the web of the rail to the bottom side of the rail. Here, a reflection of the 'rail fillet' comprises a non-correct positioning. As long as the signals do proceed via the web, the apparatus is positioned correctly.

According to the present invention, the manner of positioning is advantageously characterized by the measures of claim 33.

A first transmitter transmits at least one first positioning signal into the railhead, via the railhead top side, such that that first positioning signal is reflected via the one bottom side part of the railhead towards a first receiver. The first positioning signal is received by the first receiver. A second transmitter transmits at least one second positioning signal into the railhead, via the railhead top side, such that that second positioning signal is reflected via the other bottom side part of the railhead towards a second receiver, the second positioning signal being received by the second receiver. In particular, transmission times of the first and second positioning signal are measured and compared to one another to position at least a part of the apparatus with respect to the railhead and/or to determine the position of the central longitudinal plane of the railhead.

In this manner, for instance, ultrasonic sources and detectors, for instance the first and second transducer, can simply and accurately be positioned with respect to the railhead, for instance to subsequently carry out a flaw detection. The positioning method may, for instance, be repeated during an above-mentioned flaw detection method, or be carried out only once during the start of such a flaw detection. The positioning may further, for instance, be carried out substantially continuously.

Further elaborations of the invention are described in the subclaims. The invention will now be explained in more detail on the basis of an exemplary embodiment and with reference to the drawing, in which:

Unless explicitly stated otherwise, in this application, 'about', 'approximately', 'substantially' or similar terms are understood to mean at least a value which deviates plus 20% and minus 20% from the respective value given. In particular, unless explicitly stated otherwise, in this application, 'about', 'approximately', 'substantially' or similar terms are understood to mean at least a value which deviates plus and minus 10% from the respective value given. More in particular, unless explicitly stated otherwise, in this application, 'about', 'approximately', 'substantially' or similar terms are understood to mean at least a value which deviates plus and minus 1% from the respective value given. In the present application, same or corresponding measures are designated by same or corresponding reference symbols.

Figure 1:
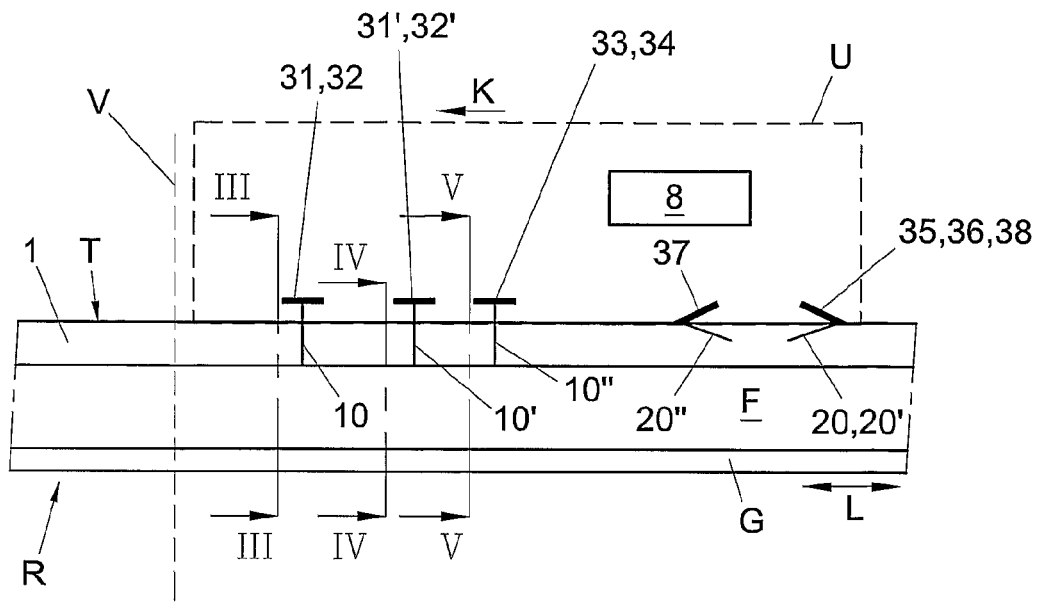
FIG. 1 shows a schematic side elevational view of an exemplary embodiment of the invention, where transmission paths of the ultrasonic signals are shown schematically.
Figure 2:
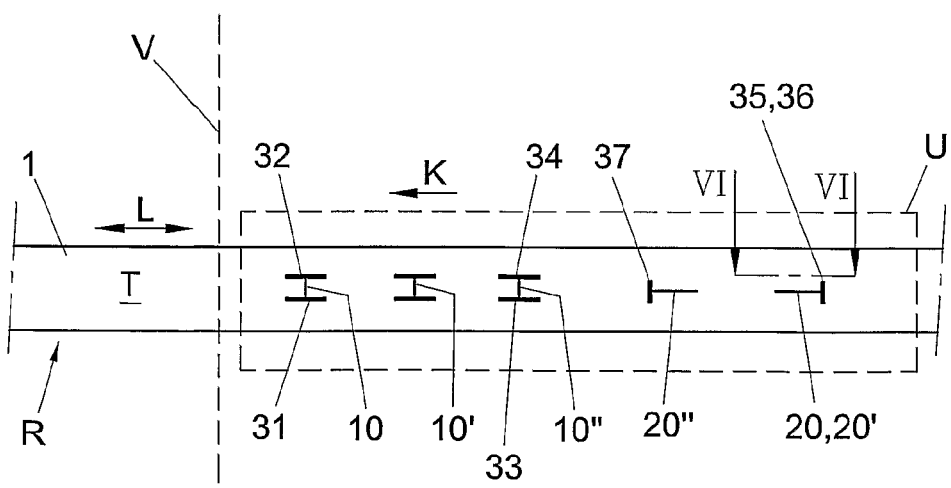
FIG. 2 shows a schematic top plan view of the side elevational view shown in FIG. 1.

FIGS. 1 and 2 schematically show an exemplary embodiment of an apparatus according to the invention. The exemplary embodiment comprises a measuring apparatus U, schematically shown by dotted lines, which is movable above a top side T of a railhead 1 of a rail R. The rail R is particularly a rail for trains. The direction of movement of the measuring apparatus U, of which one direction is designated by arrow K, is parallel to a longitudinal direction L of the rail R.

The measuring apparatus U in itself may be designed in various manners known from practice, and comprise, for instance, a measuring train, or a part thereof, an apparatus which is manually movable over the rail, and/or the like. The apparatus U may, for instance, comprise one or more roller probes (as shown in WO82/03920), but that is not necessary.

The measuring apparatus U is provided with a number of transducers 31, 32, 31', 32', 33, 34, 35, 36, 37, 38 which are arranged to introduce ultrasonic signals into the railhead 1 and to pick up echoes and/or reflected signals coming from those signals. Alternatively, for instance, other sound sources and/or sound detectors may be used to generate and/or detect ultrasonic signals. Thus, for instance, laser sources may be used for generating ultrasonic signals.

During use, the transducers 31-38 are in contact with the top side T of the railhead 1 in a suitable manner, for instance directly or indirectly, via a liquid, via air or in a different manner. The transducers are, for instance, connected to a control 8 (which is only shown schematically in FIG. 1). The control 8 is, for instance, arranged for controlling the transducers and/or processing signals received by the transducers. The control 8 may, for instance, be arranged for distinguishing transverse sound signals detected by the transducers from detected longitudinal sound signals. The control 8 is, for instance, arranged for determining, on the basis of ultrasonic signals detected by the transducers, whether and where any flaws, cracks, defects or other irregularities are located in the object, and for determining what type of flaws is involved. The exemplary embodiment may, for instance, be provided with one or more control programs, which are provided with program codes which make the control 8 at least suitable for carrying out a method according to the invention, at least after the control 8 has been loaded with the control program.

Figure 3:
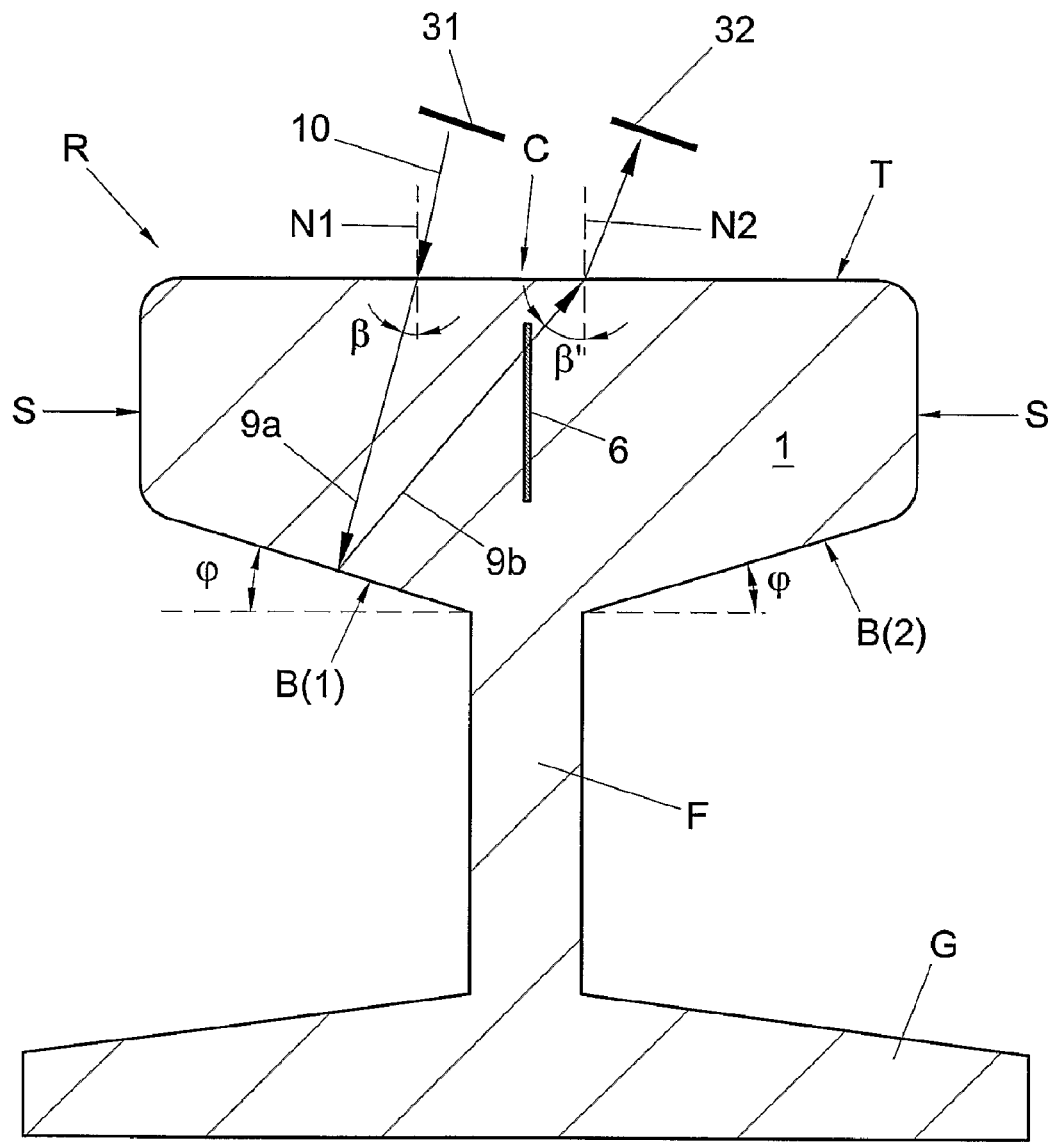
FIG. 3 shows a schematic cross-sectional view over line III-III of FIG. 1.

As FIGS. 1-3 schematically show, the railhead 1 is provided with a top side T, a bottom side B and longitudinal sides S extending between that top side T and bottom side B. Below a central center part C of the railhead 1, a vertical flange F (also called rail web) of the rail R extends, which flange F is provided with a rail base G at the end remote from the railhead 1. The head bottom side B mentioned is divided into two bottom side parts B(1), B(2) by the vertical flange F (see FIG. 3). In particular, the rail R comprises a standard, symmetrical rail section, while an extension of the railhead bottom side B and an extension of the railhead top side T, viewed in a direction away from the central railhead part C, include an angle $\phi$ which is approximately 20° (see FIG. 3). This central railhead part C is, in particular, substantially formed by the railhead part extending between the railhead top side T and the rail web F.

As FIGS. 1 and 2 show, the exemplary embodiment is provided with a first ultrasonic transducer 31 to transmit a first signal 10 into the railhead 1, via the railhead top side T. The first signal 10 may, for instance, comprise a transverse sound signal and/or a longitudinal sound signal, at least when traversing railhead 1. The exemplary embodiment is further provided with a second ultrasonic transducer 32 to receive at least a part of the first signal 10 mentioned from the railhead 1 again. As the Figures show, the first and second transducer 31, 32 are, for instance, each arranged along a virtual transverse plane of the apparatus U. This transverse plane extends substantially at right angles with respect to the direction of movement K, is operatively substantially parallel to a virtual transverse plane V of the rail R (see FIGS. 1 and 2), and accordingly intersects the rail R substantially at right angles. This virtual transverse plane of the apparatus U, along which the transducers 31, 32 can be arranged, may, for instance, include angles of approximately 90° with outsides of the rail R. The exemplary embodiment is particularly arranged for detecting flaws by means of transmission mode measurements.

As FIG. 3 shows, the first ultrasonic transducer 31 has operatively preferably been brought into such a respective first transmitting/receiving position that a respective first transmitting/receiving device extends substantially transverse to a rail longitudinal direction, and is directed slightly away from the central railhead part C. The second ultrasonic transducer 32 has preferably been brought into such a respective second transmitting/receiving position that a respective second transmitting/receiving device extends substantially transverse to a rail longitudinal direction, and is directed slightly towards the central railhead part C. Each transducer 31, 32 may, for instance be arranged so as to be able to be brought or moved between different positions, for instance between suitable positioning positions (see FIGS. 9A and 9B), while one of the positioning positions is, for instance, substantially identical to a flaw detection transmitting/receiving position shown in FIG. 3. In this positioning position, the transducers 31, 32 may, for instance, be used in a method for positioning at least a part of the measuring apparatus U, such as the transducers themselves, with respect to a centerline, or center longitudinal plane W, of the rail.

In this manner, the first and second transducer 31, 32 may, for instance, carry out a rail flaw detection, in which the first signal 10 traverses the railhead 1 only substantially in rail transverse directions and extends in a transmission plane which includes, for instance, a relatively small angle with an above-mentioned virtual transverse plane of the rail, for instance an angle which is in the range from approximately −10° to approximately 10°. This transmission plane may intersect the rail R for instance substantially transversely.

The first and second transducer 31, 32 are preferably arranged next to or near each other, for instance at a distance which is shorter than a width of the railhead 1 (see FIGS. 2 and 3).

In particular, the first transducer can operatively be brought into such a position that each first signal 10 transmitted by the first transducer 31:
  enters the railhead 1 via the head top side T;
  is only once reflected by the railhead bottom side B, and not by a longitudinal side S of the railhead 1;
  reaches at least one substantially central railhead part M; and
  can exit the railhead 1 via the head top side T;
  while the second transducer 32 mentioned is arranged for detecting the ultrasonic first signals 10 exiting the head top side T. This will be explained in more detail hereinbelow with reference to FIG. 3.

Figure 4:
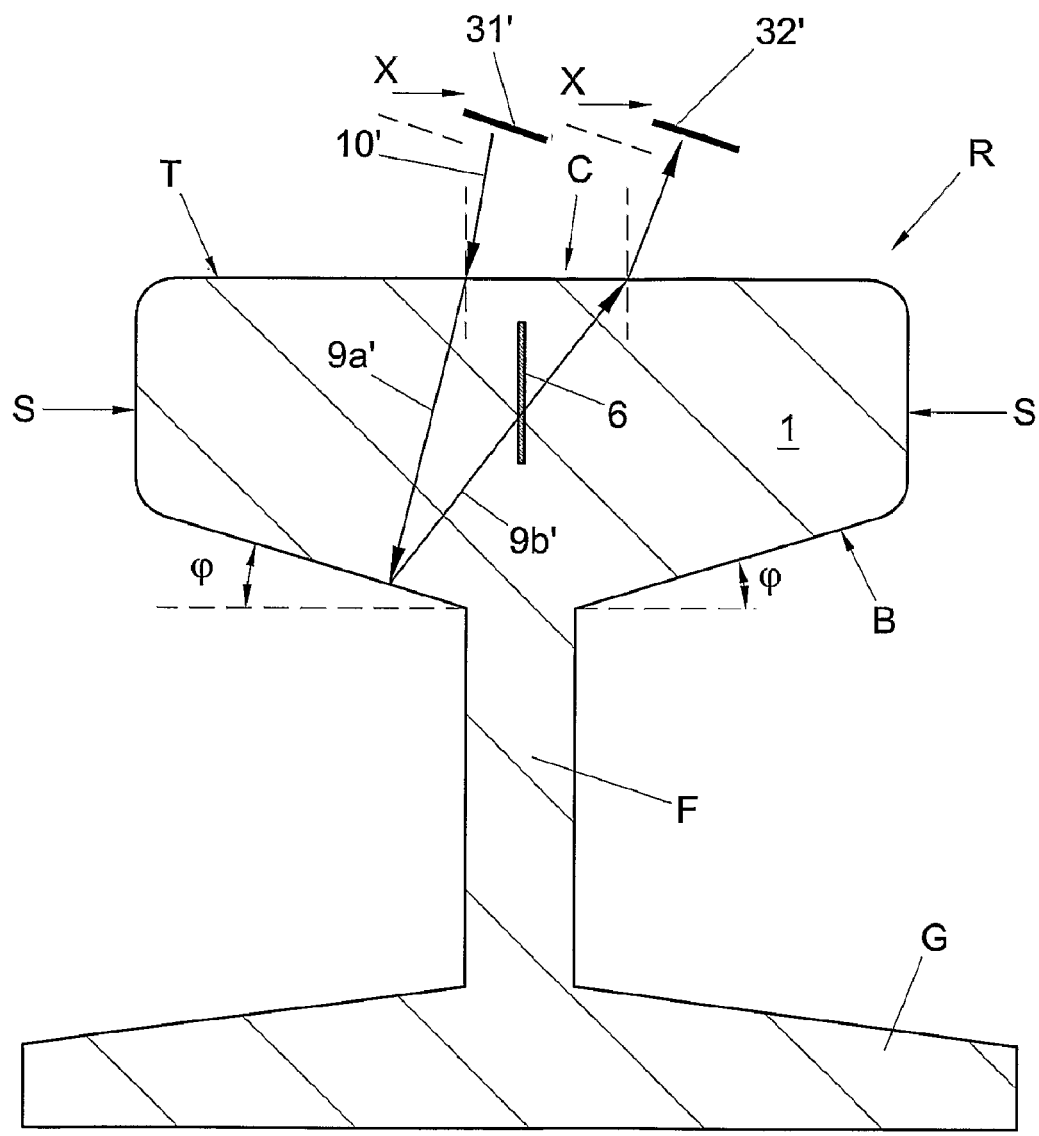
FIG. 4 shows a schematic cross-sectional view over line IV-IV of FIG. 1.

As FIGS. 1, 2 and 4 show, the apparatus U may further be provided with transducers 31', 32', which are slightly shifted in position with respect to the first and second transducers 31, 32. The operation of these transducers 31', 32' is discussed hereinbelow with reference to FIG. 4.

Figure 5:
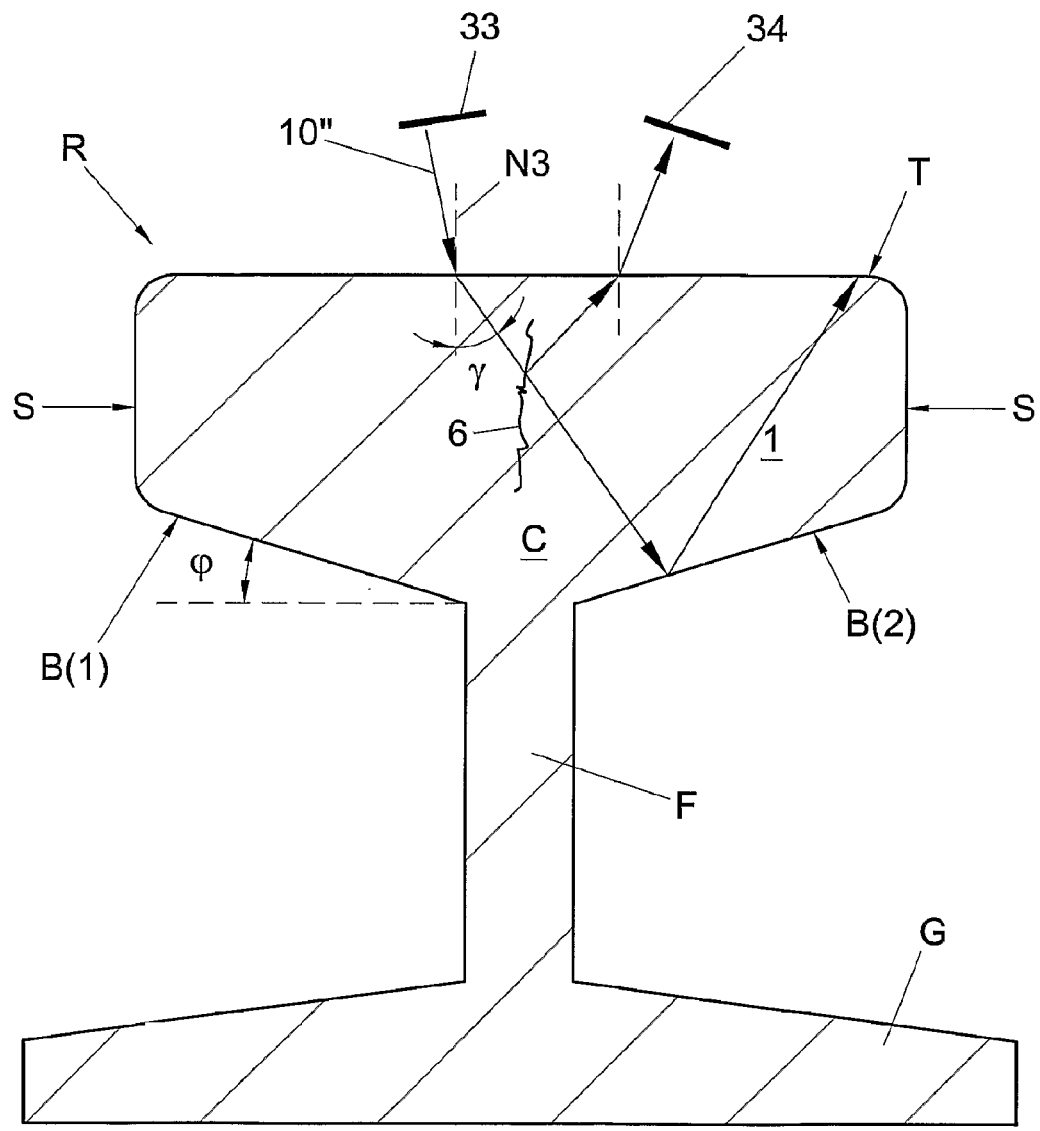
FIG. 5 shows a schematic cross-sectional view over line V-V of FIG. 1.

Further, the exemplary embodiment is provided with a third ultrasonic transducer 33 and a fourth ultrasonic transducer 34 which can operatively be brought into such a respective transmitting position and receiving position that a respective transmitting direction and respective receiving direction each extend substantially transverse to a rail longitudinal direction L, and are directed to a central railhead part C (see also FIG. 5). The third and fourth transducer 33, 34 are each also preferably arranged along a virtual transverse plane of the direction of movement K mentioned. Further, the third and fourth transducer 33, 34 are operatively preferably arranged next to or near each other, for instance also at a distance which is shorter than a width of the railhead 1. The third and fourth transducer 33, 34 are, in particular, each arranged for transmitting longitudinal sound signals through the railhead 1 and receiving ultrasonic signals coming from the railhead 1, respectively.

It is noted that, further, transverse sound signals can propagate through the railhead 1 during use of the third or fourth transducer 33, 34, under the influence of that transducer 33, 34; however, these transverse sound signals are not shown in FIG. 5. Any transverse signals can easily be distinguished from longitudinal sound signals, for instance automatically and/or by the control 8. In the first place, such a distinction can be achieved automatically in that transverse sound— which comes from a same sound source as an above-mentioned longitudinal sound signal—does not exit or hardly exits the railhead 1, or at different angles. A distinction can further be achieved by the control 8, by utilizing the fact that longitudinal sound signals will exit the railhead 1 much earlier than any corresponding transverse sound signals, because of different sound velocities. The control 8 may, for instance, each time—after transmission of a sound signal by source 33—determine a relatively short measuring period, of which it is already known that the faster longitudinal sound signals could reach the detector 34 within that measuring period. Signals which are received by the detector 34 outside the measuring period, for instance slower transverse sound signals, can then be rejected by the control 8. Any transverse sound signals will substantially be left out of account in the discussion of FIG. 5.

With the third and fourth transducer 33, 34, for instance verification measurements can be carried out, to verify measurements carried out by the first and second transducer. On the other hand, the third and fourth transducer 33, 34 may, for instance, be used independently of the first and second transducer 31, 32. In addition, conversely, the first and second transducer 31, 32 can be used for carrying out verification measurements, to verify measurements carried out by the third and fourth transducer.

In addition, the exemplary embodiment is provided with a fifth transducer 35 arranged for transmitting at least one ultrasonic second signal 20 into the railhead 1, via the head top side T mentioned, at a particular angle, substantially parallel to the head top side T mentioned, such that at least a part of the second ultrasonic signal can operatively propagate through the railhead as a creep wave near the head top side T. To this end, the second signal 20 comprises longitudinal sound, as opposed to the transverse (shear wave) sound described in U.S. Pat. No. 3,251,220. The apparatus may further be provided with a sixth transducer 36 arranged for transmitting longitudinal sound signals into the railhead 1 at a slightly smaller angle, and for instance with an eighth transducer 38 for transmitting longitudinal sound signals into the railhead 1 at still smaller angles. In addition, the fifth, sixth and eighth transducer 35, 36, 38 are each, for instance, suitable for detecting ultrasonic sound which operatively exits the head top side T.

The fifth and sixth transducer 35, 36 may, for instance, be used independently of the first, second, third and fourth transducer 31-34, or, conversely, in combination therewith, to detect flaws in the railhead 1.

FIGS. 1 and 2 further show use of one or more seventh transducers 37 which are each arranged for transmitting at least one other second signal 20" into the railhead 1 substantially in an opposite rail longitudinal direction, for forming a creep wave. This other signal 20" also comprises longitudinal sound. The at least one seventh transducer 37 may, for instance, be used instead of the fifth, sixth and/or eighth transducer mentioned, or in combination with the fifth, sixth and/or eighth transducer, for instance to detect flaws extending in different directions and/or when the exemplary embodiment is operatively moved in an opposite direction with respect to the rail R. In addition, the at least one seventh transducer 37 may, for instance, carry out a verification measurement with regard to measurements carried out by the fifth, sixth and/or eighth transducer, or vice versa.

As FIG. 1 shows, the different transducer pairs mentioned are each arranged at suitable longitudinal distances from one another, measured in a rail longitudinal direction, so that the transducer pairs can successively test a same rail part for flaws when the apparatus U is moved over that rail part.

During use of the exemplary embodiment, the railhead 1 of the rail R is tested for flaws, for instance cracks, by the apparatus U. Here, the apparatus U can be moved at a desired speed with respect to the rail R in the direction of movement K shown, or in an opposite direction.

As FIGS. 1-3 show, at least one ultrasonic first signal 10 is operatively transmitted into the railhead 1 via the head top side T mentioned, for instance by the first transducer 31. FIG. 3 shows how the first signal 10 is transmitted into the railhead 1 by the first transducer 31, in a direction directed slightly away from the central rail part C and towards the railhead bottom side B, in order to then be reflected by the railhead bottom side B towards the central railhead part C. The signal 10 thus transmitted traverses a transmission path 9, comprising an upstream path part 9a not yet reflected in the railhead, which extends from the railhead top side T to a railhead bottom side B, substantially outside the central railhead part C, and a downstream path part 9b which has been reflected in the railhead, which extends from the railhead bottom side B via the central railhead part C to the head to side T. The transmission path 9 extends in an above-mentioned virtual transmission plane, which transmission plane extends substantially transverse to the longitudinal direction L of the rail R.

As FIG. 3 clearly shows, when the first signal 10 traverses the transmission path 9, it is only once reflected by the railhead bottom side B, and not by a railhead longitudinal side S. Here, a reflected path part 9b of this first signal 10 is directed towards the central railhead part C. After the first signal 10 has exited the head top side T, the signal 10, or a part thereof, can be detected by the second transducer 32.

In one aspect of the invention, a not yet reflected signal part 9a and the normal n1 of the railhead top side T mentioned include an exit angle $\beta$ which is smaller than the angle $\phi$ included by an extension of the railhead bottom side B and the railhead top side T. This not yet reflected signal part 9a is the signal part, in the railhead 1, which has not yet reached the bottom side B of the railhead 1. This not yet reflected signal part 9a and the normal n1 of the railhead top side T mentioned may, for instance, include an exit angle $\beta$ which is smaller than approximately 20°. An above-mentioned exit angle $\beta$ may, for instance, be approximately half of the angle $\phi$ mentioned which is included by an extension of the railhead bottom side B and an extension of the railhead top side T, for instance approximately 10°. It is found that, with this exit angle, particularly good results can be obtained, in particular with a rail which is provided with a standard rail section. Here, the first signal 10 traverses the center part C of the railhead to be tested only once, and covers a particularly short distance. In addition, in this manner, the first signal 10 can relatively simply be introduced into the railhead 1, via the rail top side.

Alternatively, the transmission path 9 is traversed by a first signal 10 in reverse order, while the second transducer 32 is used as a transmitter and the first transducer 31 as a receiver. In that case, the first signal 10 is transmitted from the railhead top side T to the central railhead part C, to then be able to reach the railhead bottom side B for the purpose of reflection. A not yet reflected signal part of the first signal 10 and a normal n2 of this railhead top side T may then, for instance, include an exit angle $\beta'$ which is slightly larger than the angle $\phi$ included by an extension of the railhead bottom side B and an extension of the railhead top side T. The latter exit angle $\beta'$ may, for instance, comprise approximately 30°, or another suitable angle (see FIG. 3).

As FIG. 3 shows, a substantially vertical railhead longitudinal flaw 6, extending in a rail longitudinal direction, will be able to bring about an interference of the transmission of the first ultrasonic signal 10, which can result in the signal detected by the second (or, alternatively, first) transducer wholly or partly falling away. In this manner, such flaws can accurately be detected. The accuracy of the flaw detection is relatively high, because the first signal 10 only needs to cover a relatively short distance through the railhead 1, and because, in addition, the first signal is only once reflected on a railhead side, namely on the railhead bottom side B.

Preferably, further, verification measurements are carried out, for instance by means of the transducers 31', 32' whose positions are slightly shifted over a horizontal transverse direction X with respect to the first and second transducer 31, 32 mentioned, as is shown in FIG. 4. Signals 10' transmitted and received by these shifted transducers 31', 32' traverse correspondingly shifted transmission paths 9', so that, therewith, a slightly different part of the central railhead C can be tested for flaws, for instance to verify a flaw detection carried out by the first and second transducer 31, 32 by means of main signals 10. Further, these transducers 31', 32', whose positions differ slightly from those of the first and second transducer 31, 32, may, for instance, be used to test another part of the central railhead part C for flaws, and/or a railhead part which is located right next to the central part C, while maintaining the advantages mentioned.

FIG. 5 shows a different method for detecting flaws in the central railhead part 1, which method is, for instance, suitable for verifying a flaw detection carried out by the first and second transducer 31, 32 mentioned. The method shown in FIG. 5 may, in addition, for instance, be independent of the first and second transducer 31, 32. As FIG. 5 shows, to this end, by the third transducer 33 mentioned, a first longitudinal sound signal 10" is transmitted into the railhead 1, towards the central head part C. In one aspect of the invention, the not yet reflected part of that first longitudinal sound signal 10" and a normal n3 of the railhead top side T include an exit angle γ which is preferably approximately 30°. It has been found that such an exit angle γ yields surprisingly good and reliable results. If, in this case, no vertical longitudinal flaw is present in the central railhead part C, the first longitudinal sound signal 10" may, for instance, reach the head bottom side B in order to be reflected, for instance such that the reflected signal part can, for instance, be detected by the first transducer. In that case, it will take a certain transmission period before that signal 10" has reached the fourth transducer after transmission. When a flaw 6 is present, then at least a part of the first verification signal 10" can be reflected and/or converted by the flaw 6 and be transmitted towards the fourth transducer 34, which may result in, for instance, an easily detectable shorter above-mentioned transmission period.

On the other hand, the longitudinal sound signal mentioned may be reflected by the railhead bottom side B mentioned so that the reflected signal part exits the railhead 1 at a distance from the central rail part C mentioned, for instance such that that signal is substantially not received by the transducer/detector 34. This is schematically shown in FIG. 5. In that case, detection of an exiting signal 10" is a good indication that a vertical longitudinal flaw 6 is present on that location in the railhead 1. Then, the fourth transducer 34 not receiving ultrasonic sound is an indication that no vertical longitudinal flaw is present.

As mentioned in the above, any occurring transverse signals can easily be operatively distinguished from the longitudinal sound signals 10", for instance automatically, like as a result of exit angles of the signals, and/or by the control 8.

The measurement data obtained by the third and fourth transducer 33, 34 may, for instance, be combined with measurement data from the first and second transducer 31, 32 to complement one another, so that an optimal detection of vertical longitudinal flaws 6 can be achieved. Signals 10 generated and received by the first and second transducer 31, 32 may, for instance, comprise main detection signals, while then the signals 10" used by the third and fourth transducer 33, 34 serve as verification signals. Of course, these transducer pairs 31, 32 and 33, 34 may also be used in a reverse order and/or function.

Figure 6:
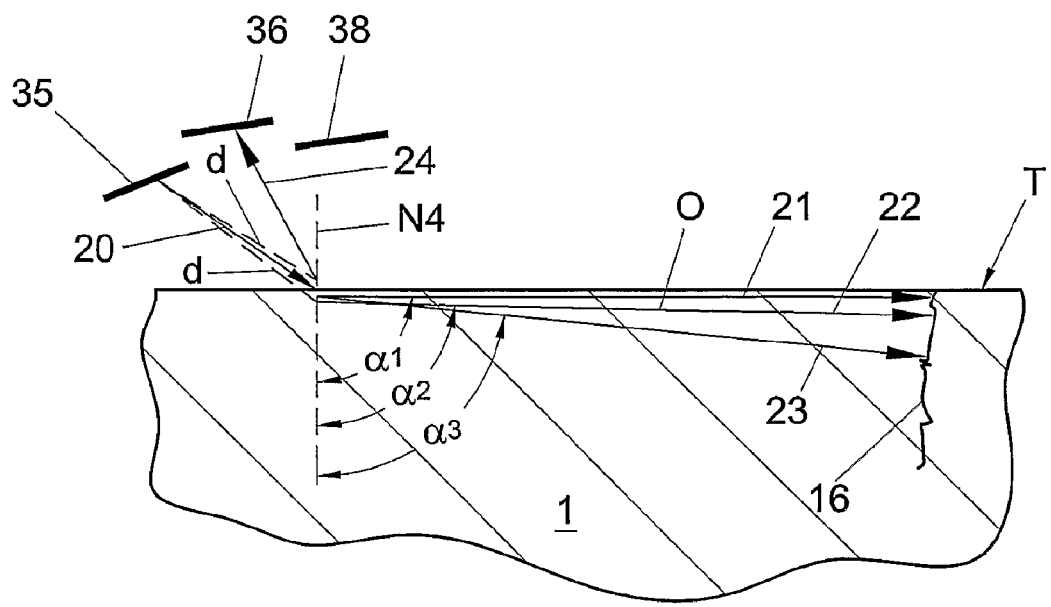
FIG. 6 shows a schematic cross-sectional view over line VI-VI of FIG. 1, where the fifth transducer operates as a transmitter and the sixth transducer as a receiver.

In one aspect of the invention, the fifth and sixth transducer 35, 36 mentioned are used to detect vertical transverse flaws 16. As FIG. 6 shows, here, the fifth transducer 35 transmits at least one ultrasonic second longitudinal sound signal 20 into the railhead 1 via the head top side T mentioned substantially parallel to the head bottom side B, in longitudinal rail direction, such that at least a part of the second ultrasonic longitudinal sound signal 20 can propagate through the railhead 1 as a creep wave 21 near the head top side T. A not yet reflected or converted signal part of the creep wave 21 includes an exit angle α1 with a normal n4 of the railhead top side T of 90°. The creep wave 21 is little disturbed by interferences of the rail surface B. The creep wave 21 can be incident on a transverse rail flaw 16 at substantially right angles, in order to be, for instance, reflected back to the sixth transducer 36 by the rail flaw 16.

As FIG. 6 shows, the fifth transducer 35 may, for instance, transmit third longitudinal sound signals 22, 23 into the railhead with exit angles α1 which are smaller than 90°. Such signals 22, 23 may then also be reflected by the vertical transverse flaw 16 and, for instance—after exiting—be detected by the sixth transducer 36. Exit of the latter signals 22, 23 is shown by arrow 24 in FIG. 6.

The fifth transducer 35 may, for instance, transmit a divergent longitudinal sound signal 20, of which certain parts can form the creep wave 21 mentioned and other parts form the third longitudinal sound signals 22, 23 mentioned. A main axis O of such a divergent signal 20 may, for instance, include an exit angle α2 with the normal n4 of the railhead top side T of approximately 85°, or a different angle. Such a fifth transducer 35 may, for instance, be provided with a relatively small crystal, in to provide a signal 20 having a divergence suitable for creep wave formation, with the respective exit angle α2. Divergence of a signal 20 transmitted by the fifth transducer 35 is shown by dotted lines d in FIGS. 6 and 7.

Figure 7:
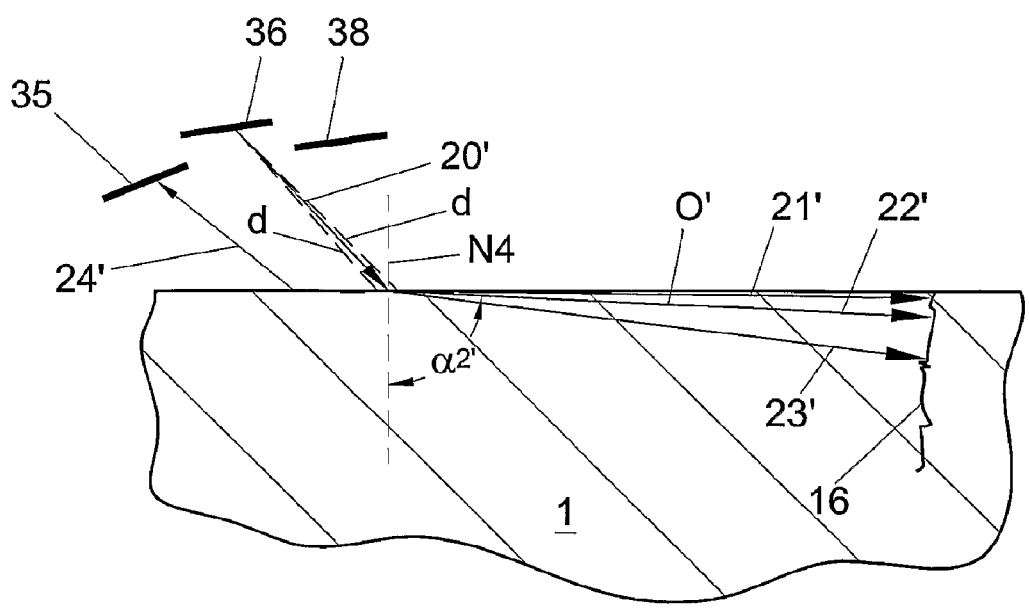
FIG. 7 shows a similar view to FIG. 6, where the sixth transducer operates as a transmitter and the fifth transducer as a receiver.

Preferably, at least two different ultrasonic divergent second signals 20, 20' are transmitted into the railhead top side T at different angles, see FIGS. 6 and 7. Thus, the sixth transducer 36 may, for instance, transmit a divergent second signal 20' into the railhead, at a slightly smaller angle of incidence than that of the signal 20 transmitted by the fifth transducer 35, such that parts 21', 22', 23' of that second signal 20' can be reflected under the influence of a transverse flaw 16, and then be detected—after exiting—by, for instance, the fifth transducer 35 and/or sixth transducer 36 mentioned. A main axis O' of such a divergent signal may, for instance, include an exit angle α2' with the normal n4 of the railhead top side T of approximately 70°, or a different angle.

The signal transmitted by the sixth transducer 36 preferably also diverges such that it results in both creep wave parts 21' and 'normal' longitudinal sound parts 22', 23' in the railhead 1 (see FIG. 7). In that case, for instance, reflected wave parts may again be detected by the fifth 35, sixth 36 or eighth transducer 38 (which is shown in FIG. 7).

As FIGS. 6 and 7 show, in addition, more transducers (one of which is designated by 38) may be arranged near the fifth and sixth transducer 35, 36 to transmit ultrasonic longitudinal sound signals into the railhead 1 and/or to receive reflected ultrasonic signals from that head again.

Further, each time, the one transducer 35, 36 or 36, 38 can transmit a signal, of which a part reflected in the railhead 1 can be received by a nearby transducer 36, 35 or 38, 36. This is found to offer a particularly reliable detection method for detection of transverse flaws 16. On the other hand, a signal transmitted by a transducer 35, 36, 37, 38 may, for instance, be partly reflected back to that transducer again by a transverse flaw 16.

In the exemplary embodiment of FIGS. 6 and 7, detection of an ultrasonic signal exiting the railhead 1 can give a good indication that a transverse vertical flaw 16 is present in the railhead 1. Because creep waves 21, 21' are used therewith, in addition, transverse flaws which are usually difficult to detect, which are located just below the rail surface, can be detected well.

As mentioned in the above, during use, in addition, for instance, an above-mentioned seventh transducer 37 can be used to transmit at least one other second signal 20" in to the railhead 1 substantially in an opposite rail longitudinal direction for forming a respective creep wave, for instance when the measuring apparatus U is moved over the rail R in an opposite direction (see FIG. 2), and/or to detect flaws extending in particular directions.

Figure 8:
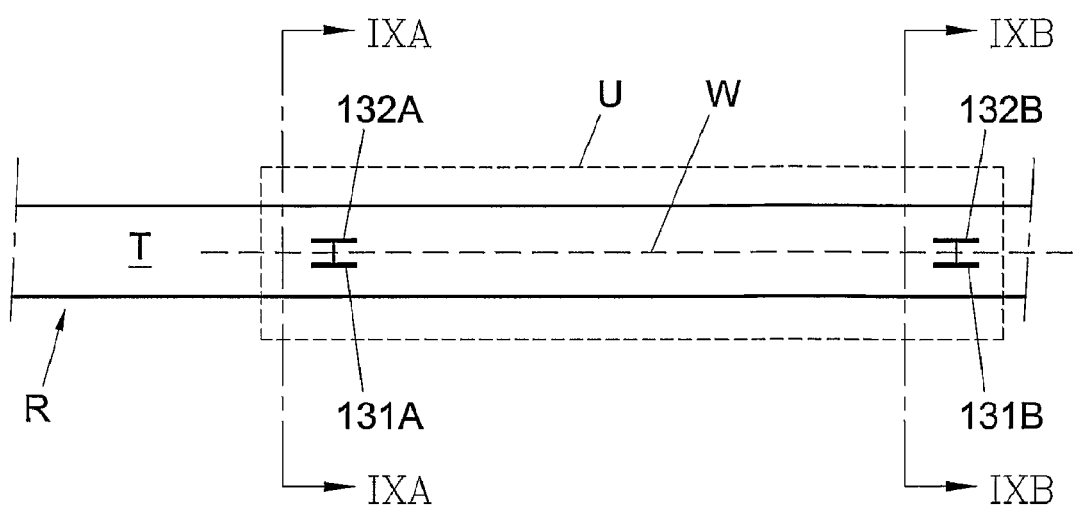
FIG. 8 shows a similar top plan view to FIG. 2, of an exemplary embodiment which is provided with a positioning assembly.
Figure 9A:
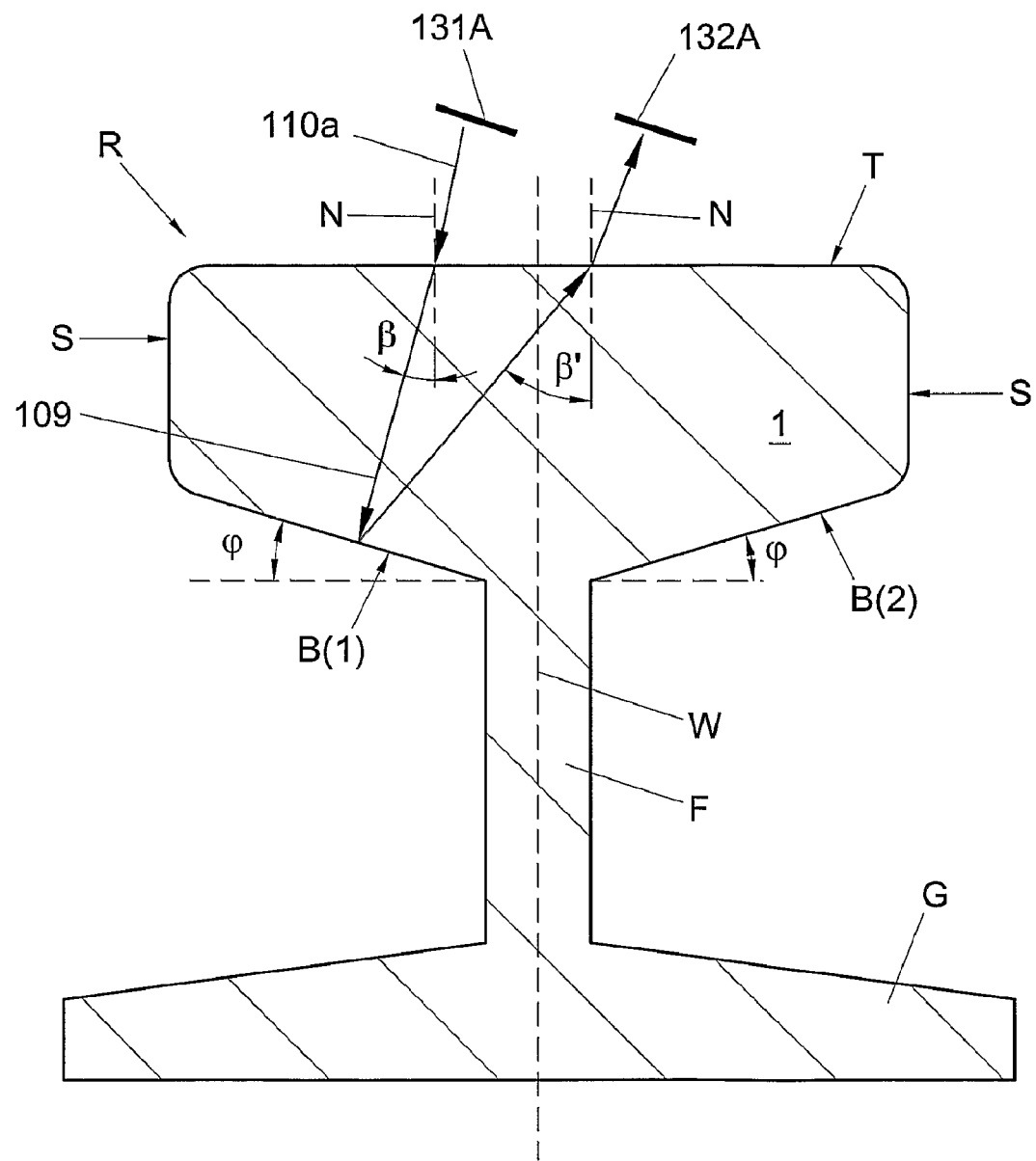
FIGS. 9A and 9B show cross-sectional views over lines IXA and IXB, respectively, of FIG. 8.
Figure 9B:
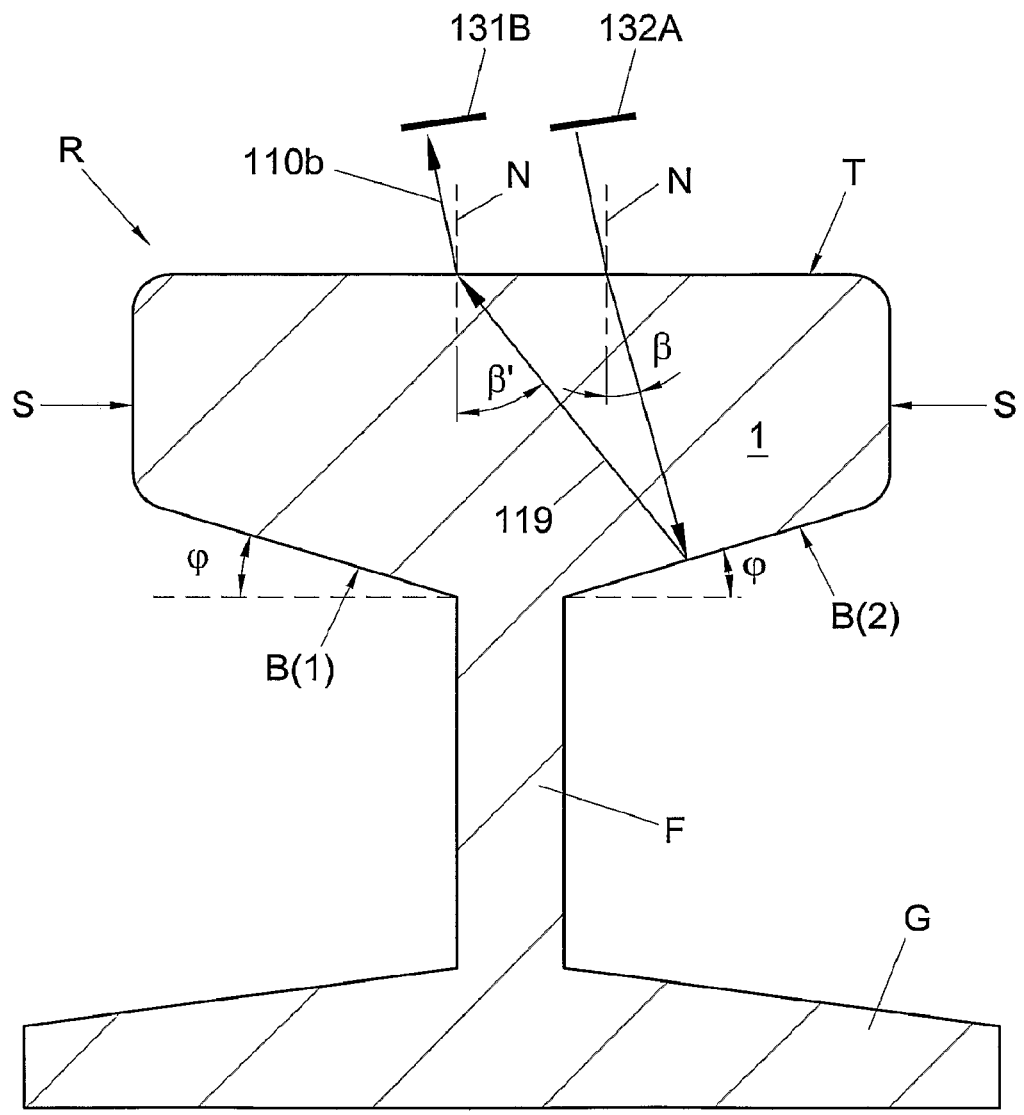

FIGS. 8, 9A and 9B schematically show a design of a measuring apparatus U, which is provided with positioning means, for instance to position the measuring apparatus and/or components of the measuring apparatus with respect to the center of the railhead, and/or to accurately determine where the center, at least a central plane W, of the railhead is located. The measuring apparatus U shown in FIGS. 8-9 may, for instance, be provided with one or more of the above-mentioned means 8, 31-38 shown in FIGS. 1-7 for detecting flaws in the rail R. For the sake of clarity of the drawing, such means 8, 31-38 are not shown in FIG. 8.

FIGS. 8-9 particularly show use of a positioning assembly, which is provided with a number of transmitters and receivers, preferably transducers, to transmit ultrasonic positioning signals 110a, 110b into the railhead and to receive them from the railhead again. In the present exemplary embodiment, the assembly is provided with a first transmitter 131A and a first receiver 132A, and a second transmitter 131B and second receiver 132B arranged at a distance therefrom. Preferably, the first transmitter 131A and first receiver 132A are mutually at substantially the same distance as the mutual distance between the second transmitter 131B and second receiver 132B. Further, the transmitters 131A, 131B and receivers 132A, 132B are, during use, preferably at substantially the same vertical distance above the rail surface T.

In particular, the assembly is designed such that a first positioning signal 110a can operatively be transmitted by the first transmitter 131A via the one railhead bottom side part B(1) to the first receiver 131B, which is shown in FIG. 9A. FIG. 9B shows that a second positioning signal 110b can be transmitted by the second transmitter 12A via the other railhead bottom side part B(2) to the second receiver 132B. Preferably, the transmission path 119 of second positioning signal 110b, through the railhead, is a mirror image of the transmission path 109 of the first positioning signal 110a, with respect to the center longitudinal plane W of the rail, at least with a desired positioning of, for instance, the apparatus U with respect to the rail.

The positioning assembly is preferably provided with a processor or control 8 for comparing transmission times of the first positioning signal and second positioning signal. The transmitters and receivers 131A, 131B, 132A, 132B can, for instance, be positioned with respect to a center of the rail on the basis of the comparison of these transmission times.

The transmitters and receivers 131A, 131B, 132A, 132B may be provided in different manners, and may, for instance, each comprise a suitable transducer. In a further elaboration of the invention, for instance, a transducer pair shown in FIG. 3 or 4 may also be used as a positioning transmitter/receiver pair 131, 132, for transmitting an above-mentioned first positioning signal into the rail and to receive it from the rail again. An above-mentioned first signal 10 for the purpose of flaw detection may, for instance, also serve as an above-mentioned positioning signal 110.

As FIG. 9A shows, the first transmitter and receiver 131A, 132A are preferably in such a first positioning position that the first transmitter 131A can transmit a first positioning signal 110a into the railhead, and such that that first positioning signal 110a is reflected via the one bottom side part B(1) (the left one in FIG. 9) of the railhead towards the first receiver 132A. The first positioning signal can then be received by the first receiver 132A.

As FIG. 9B shows, the second transmitter 131B and second receiver 132B may be arranged for transmitting a second positioning signal 110b via the other bottom side part B(2) (the right one in FIG. 9) of the railhead. Here, the second transmitter 131B preferably transmits the second positioning signal 110b into the railhead such that the second positioning signal 110b includes an exit angle $\beta$, $\beta'$ with a normal N of the railhead top side T, which exit angle is equal to the one between the first positioning signal and a normal N of the railhead top side T (see FIGS. 9A and 9B). The angle of incidence of the second positioning signal 110b on the top side T of the rail is preferably equal to the angle of incidence of the first positioning signal 110a on that top side T. It further follows from FIGS. 3 and 8A that the transmission part of, for instance, the first positioning signal 110a can be identical to the transmission path 109 of the first signal 10 shown in FIG. 3.

As FIG. 9B shows, the second transmitter 131B may, for instance, transmit a second positioning signal 110b into the railhead, towards the second receiver 132B. The second positioning signal 110b traverses the railhead, for instance, substantially in opposite direction with respect to the first positioning signal 110a. Here, the second positioning signal can be reflected via the other bottom side part B(2) (the right one in FIG. 9) of the railhead towards the second receiver 132B, and be received by the second receiver 132B.

Each positioning signal 110a, 110b is preferably transmitted such that that signal 110a, 110b is substantially only once reflected by the railhead bottom side B, and not by the railhead longitudinal side S, and can exit again via the head top side T after reflection. Not yet reflected positioning signal parts and normals N of this railhead top side T may, for instance, include the exit angles $\beta$ or $\beta'$ mentioned, which angles are slightly smaller and slightly larger, respectively, than the angle $\phi$ included by an extension of the railhead bottom side B and an extension of the railhead top side T.

The positioning signals 110a, 110b, for instance, traverse transmission paths extending substantially transverse with respect to the longitudinal direction L of the rail, like above-mentioned ultrasonic first signals 10.

With a particular positioning of the positioning transmitters and positioning receivers 131a, 132A, 131B, 132B with respect to the rail (which positioning is shown in FIGS. 8-9), in which these transmitters and receivers are, for instance, located at substantially equal lateral (in the Figures horizontal) distances with respect to the central (in the Figures vertical) longitudinal plane W of the rail, and at a substantially equal distance (vertically) above the rail top side T, transmission paths of a first and second positioning signal 110a, 110b will usually be equally long (at least with a substantially symmetrical railhead, and, for instance, when the first and second transmitter are substantially identical, and when the first and second receiver are substantially identical). With a different positioning with respect tot her rail, in which the transmitters and receivers 131, 132 are, for instance, not located at an equal lateral distance with respect to the central longitudinal plane W of the rail, but are still at a substantially equal distance above the rail top side T, transmission paths of these positioning signals 110a, 110b will usually not be equally long, which is simply measurable via transmission time measurements.

The detection of the positioning signals 110a, 110b may simply be used, for instance by an above-mentioned control or processor 8, to position a respective measuring apparatus U or a part thereof, the ultrasonic sound sources mentioned and/or the detectors mentioned with respect to the railhead. In particular, the transmission times of the first and second positioning signal can simply be measured and by compared with one another by such a processor in order to position, for instance, the apparatus, above-mentioned transducers and/or the positioning means substantially symmetrical with respect to the railhead, or to position them otherwise. Further, the positioning signals may be used to determine or trace the position of the centerline of the railhead. In addition, the apparatus may be designed to determine the height of the railhead from the positioning signals, and/or to detect changes in the height of the railhead. In this manner, for instance rail wear can be measured.

The positioning method shown in FIGS. 8-9 is well suitable for use in/by an apparatus U for detecting flaws in a railhead, but may also be used for other uses. This positioning method may, for instance, be carried out before an above-mentioned flaw detection shown in FIGS. 1-7 is carried out, and/or be part of the flaw detection method. The positioning method may, for instance, be carried out by an above-mentioned first and second transducer and/or by other transducers, while the transducers can be brought, or have already been brought, to the suitable positioning positions shown in FIG. 8.

Thus, the method shown in FIGS. 9A-9B may, for instance, be carried out by four or more transducers, namely a pair of transducers 131A, 132A for transmitting and receiving a first positioning signal 110a, and a pair of transducers 131B, 132B for transmitting and receiving a second positioning signal 110b. Alternatively, the positioning method may, for instance, utilize one pair of transducers, which are movable between suitable positioning positions, to first transmit positioning signals via the one bottom side part B(1) of the railhead towards one another, and then via the other railhead bottom side part B(2). In that case, each transducer can act both as a transmitter and receiver.

It goes without saying that the invention is not limited to the exemplary embodiment described. Various modifications are possible within the framework of the invention as set forth in the following claims.

Thus, the transducers mentioned and the like may each be designed and arranged in various manners. Transducers may, for instance, be arranged in one or more array formations, in which different transducers are, for instance, arranged to transmit and/or receive signals at different angles.

A transducer may, for instance, be used in a single mode (transmitting or receiving), or in a dual mode (transmitting and receiving), which, for instance, depends on the design of the transducer.

Further, instead of transducers, for instance, other means can be used to generate and/or detect the ultrasonic signals.

Further, the ultrasonic signals mentioned may each in themselves show a certain form of beam scattering, or divergence.

The invention claimed is:

1. A method for detecting flaws in a railhead of a rail, the railhead having a top side, a bottom side and longitudinal sides extending between said top side and said bottom side, the method comprising:
    transmitting at least one ultrasonic first signal into the railhead via said railhead top side, said at least one ultrasonic first signal traversing a transmission path that extends in a virtual transmission plane extending substantially transverse to a longitudinal direction of the rail so that:
        the at least one ultrasonic first signal is reflected by the railhead bottom side only once, and without being reflected by a railhead longitudinal side,
        the reflected ultrasonic first signal reaches at least one substantially central railhead part, and
        the reflected ultrasonic first signal exits the railhead via the railhead top side; and
    detecting reflected ultrasonic first signals exiting the railhead top side.

2. A method according to claim 1, wherein said transmission plane includes an angle with a virtual transverse plane of the rail which is in the range from approximately −10° to approximately 10°, wherein said transmission plane is a virtual transverse plane or substantially a virtual transverse plane of the rail.

3. A method according to claim 1, wherein an incident or unreflected path part of a said at least one ultrasonic first signal is directed slightly away from the at least one substantially central railhead part, and wherein a reflected path part of said reflected ultrasonic first signal is directed towards the at least one substantially central railhead part, or vice versa.

4. A method according to claim 1, wherein said at least one ultrasonic first signal is transmitted from the railhead top side to the railhead bottom side, to then be reflected by the railhead bottom side towards the at least one substantially central railhead part.

5. A method according to claim 4, wherein an incident or unreflected signal part of the at least one ultrasonic first signal and a normal of said railhead top side include an exit angle ($\beta$) which is smaller than an angle ($\phi$) included by an extension of the railhead bottom side and an extension of the railhead top side.

6. A method according to claim 4, wherein an incident or unreflected part of said at least one ultrasonic first signal and a normal of said railhead top side include an exit angle ($\beta$) of less than approximately 20°.

7. A method according to claim 6, wherein said exit angle ($\beta$) is approximately 10°.

8. A method for detecting flaws in a railhead of a rail according to claim 1 further comprising:
    transmitting at least one ultrasonic longitudinal sound signal into the railhead from the railhead top side to the railhead bottom side via the at least one substantially central railhead part,
    wherein a transmission path of the at least one ultrasonic longitudinal sound signal extends in a virtual transmission plane that extends transverse or substantially transverse to a longitudinal direction of the rail; and
    detecting reflected ultrasonic longitudinal sound signals exiting the railhead top side using at least one detector.

9. A method according to claim 8, wherein an incident or unreflected part of said at least one longitudinal sound signal and a normal of said railhead top side include an exit angle ($\gamma$) which is approximately 30°.

10. A method according to claim 8, wherein said railhead bottom side reflects said at least one longitudinal sound signal so that a reflected signal part exits the railhead at a distance from said at least one substantially central railhead part, without said reflected signal part being substantially received by any of said at least one detector.

11. A method according to claim 8, wherein transmitting includes:
    transmitting at least one ultrasonic first main signal from the railhead top side to the railhead bottom side;
    reflecting said at least one ultrasonic first main signal by the railhead bottom side towards said substantially central railhead part; and
    transmitting at least one ultrasonic first verification signal from the railhead top side to the railhead bottom side through the at least one substantially central railhead part.

12. A method according to claim 8, wherein an extension of the railhead bottom side and an extension of the railhead top side, viewed in a direction away from the at least one substantially central railhead part, include an angle ($\phi$) which is approximately 20°.

13. A method for detecting flaws in a railhead of a rail according to claim 1, the method further comprising:
    transmitting at least one ultrasonic longitudinal sound signal into the railhead via said railhead top side so that at least a part of the at least one longitudinal sound signal propagates through the railhead as a creep wave near the railhead top side, and
    detecting at least one reflected creep wave part that exits the railhead top side after being reflected back from the railhead.

14. A method according to claim 13, wherein at least two different ultrasonic longitudinal sound signals are transmitted into the railhead top side at different angles.

15. A method according to claim 13, wherein transmitting at least one ultrasonic longitudinal sound signal includes:
    transmitting a first longitudinal sound signal into the railhead in a first rail longitudinal direction to form at least one respective creep wave, and
    transmitting a second longitudinal sound signal into the railhead in a second rail longitudinal direction that is substantially opposite the first rail longitudinal direction, to form at least one respective creep wave.

16. A method according to claim 1, wherein a plurality of said at least one ultrasonic first signals is used as positioning signals, to position at least a part of a measuring apparatus with respect to the railhead and/or to determine a position of a center plane of the railhead.

17. A method according to claim 1, wherein said railhead bottom side is separated into a first bottom side part and a second bottom side part by a rail flange, the method further comprising:
    transmitting a first positioning signal into the railhead from a first transmitter such that a first positioning signal is reflected by the first bottom side part of the railhead towards a first receiver;
    receiving the reflected first positioning signal at the first receiver;
    transmitting a second positioning signal into the railhead from a second transmitter such that a second positioning signal is reflected by the second bottom side part of the railhead towards a second receiver;
    receiving the reflected second positioning signal at the second receiver; and
    measuring transmission times of the reflected first positioning signal and the reflected second positioning signal and
    comparing the transmission times to one another, to position the first and second transmitters and the first and second receivers and/or a measuring apparatus with respect to the railhead.

18. An apparatus for detecting flaws in a railhead of a rail, that is structured and arranged for carrying out a method according to claim 1.

19. An assembly for use with a rail having a railhead with a top side and a bottom side, the assembly comprising:
    an apparatus for detecting flaws in the railhead, wherein the apparatus is movable over the top side of the railhead, in a particular direction of movement which is parallel to a rail longitudinal direction, the apparatus including:
        at least one first ultrasonic sound source that is operatively disposed at a location on the railhead of the rail from which corresponding first ultrasonic sound signal is transmitted and that:
            enters the railhead via the railhead top side;
            is only once reflected by the railhead bottom side, without being reflected by a longitudinal side of the railhead;
            reaches at least one substantially central railhead part; and
            exits the railhead via the railhead top side; and
        at least one first detector that is structured and arranged to detect corresponding reflected first ultrasonic signals exiting the railhead top side.

20. An assembly according to claim 19, wherein said first ultrasonic sound source and said first detector are each arranged substantially along a virtual transverse plane of said direction of movement.

21. An assembly according to claim 19, wherein said first ultrasonic sound source and said first detector are disposed relative to one another at a distance that is shorter than a width of the railhead.

22. An assembly according to claim 19, wherein the first ultrasonic sound source is disposed at a transmitting location at which a respective transmitting direction is directed slightly away from the at least one substantially central railhead part; and
    wherein the first detector is disposed at a corresponding receiving location at which a respective receiving direction is directed towards the at least one substantially central railhead part.

23. An assembly according to claim 19, wherein said railhead bottom side includes a rail flange that separates the bottom side of the railhead into a first bottom apart and a second bottom part,
    wherein the assembly further comprises:
    a plurality of transmitters to transmit first and second positioning signals into the railhead,
    a plurality of receivers to receive corresponding reflected first and reflected second positioning signals from the railhead, such that a first positioning signal can be transmitted by a first transmitter via the first bottom side part to a first receiver, and that a second positioning signal can be transmitted by a second transmitter via the second bottom side part to a second receiver; and
    a processor to compare transmission times of the reflected first positioning signal and the reflected second positioning signal, wherein the processor is adapted to determine a disposition of at least a part of the flaw-detecting apparatus with respect to a center of the rail based on a comparison of said transmission times.

24. An assembly according to claim 19 wherein:
at least one of said first ultrasonic sound source is an ultrasonic longitudinal sound source that is adapted to transmit ultrasonic longitudinal sound; and
at least one of said first detector is a receiver that is adapted to detect ultrasonic sound,
wherein the ultrasonic longitudinal sound source is disposed in a corresponding transmitting position such that a respective transmitting direction extends substantially transverse to a rail longitudinal direction and is directed to at least one substantially central railhead part, and
wherein the receiver is disposed in a corresponding receiving position such that a respective receiving direction extends substantially transverse to the rail longitudinal direction, and is directed to the at least one substantially central railhead part.

25. An assembly according to claim 24, wherein said longitudinal sound source and the receiver are each arranged along a virtual transverse plane of said direction of movement, and
wherein the longitudinal sound source and the receiver are operatively arranged with respect to each other at a distance that is shorter than a width of the railhead.

26. An assembly according to claim 19, wherein each of said at least one first ultrasonic sound source is adapted for transmitting at least one ultrasonic longitudinal sound signal into the railhead via said railhead top side, such that at least a part of the longitudinal sound signal propagates through the railhead as a creep wave near the railhead top side.

27. An assembly according to claim 26, provided with at least two sound sources to transmit at least two different ultrasonic longitudinal sound signals into the railhead top side at different angles.

28. An assembly according to claim 26, wherein the at least one first detector is adapted for detecting at least one of ultrasonic signals and creep wave parts, which have operatively been reflected in the railhead and exit the railhead top side.

29. An assembly according to claim 26, wherein each of the at least one first ultrasonic sound source includes;
at least one first sound source that is structured and arranged for transmitting at least one ultrasonic longitudinal sound signal into the railhead substantially in a first rail longitudinal direction to form respective creep wave; and
at least one second sound source that is structured and arranged for transmitting at least one other ultrasonic longitudinal sound signal into the railhead substantially in an opposite rail longitudinal direction to form a respective creep wave.

30. A control program that is disposed on a computer-readable medium, executable on a controller, and provided with program codes that make the controller at least suitable for carrying out the method according to claim 1, after the controller has been loaded with the control program for the purpose of controlling one or more sound sources and detectors.

31. An apparatus for detecting flaws in a railhead of a rail, being an apparatus of an assembly according to claim 19.

32. Use of an apparatus according to claim 31 for testing rails for defects.

33. A method for positioning an apparatus with respect to a railhead of a rail and/or for determining a position of a central longitudinal plane of the railhead, the railhead having a top side, a bottom side, and longitudinal sides extending between said top side and said bottom side, wherein said railhead bottom side is separated by a flange into a first bottom part and a second bottom part, the method comprising:
transmitting at least one first positioning signal from a first transmitter into the railhead via the railhead top side, such that said first positioning signal is reflected via a first bottom side part of the railhead towards a first receiver;
receiving the first positioning signal at the first receiver;
transmitting at least one second positioning signal from a second transmitter into the railhead, via the railhead top side, such that said second positioning signal is reflected via a second bottom side part of the railhead towards a second receiver;
receiving the second positioning signal at the second receiver;
measuring and comparing transmission times of the first and second positioning signal with one another; and
positioning at least a part of the apparatus with respect to the railhead and/or determining the position of a central longitudinal plane of the railhead.

34. A method according to claim 33, wherein during the transmitting step:
an incident or unreflected path part of a said first signal is directed slightly away from the at least one central railhead part, wherein a reflected path part of said first signal is directed towards the at least one central railhead part, or vice versa;
at least one said ultrasonic first signal is transmitted from the railhead top side to the railhead bottom side and reflected by the railhead bottom side towards the at least one central railhead part;
an incident or unreflected signal part of the first signal and a normal of said railhead top side include an exit angle which is smaller than an angle included by an extension of the railhead bottom side and an extension of the railhead top side;
an incident or unreflected part of said first signal and a normal of said railhead top side include an exit angle being at least one of less than approximately 20° and approximately 10°.

35. A method for detecting flaws in a railhead of a rail according to claim 34, wherein the each of the at least one ultrasonic first signal is an ultrasonic longitudinal sound signal, the transmitting and receiving steps including:
an incident or unreflected part of said longitudinal sound signal and a normal of said railhead top side include an exit angle which is approximately 30';
reflecting said longitudinal sound signal by said railhead bottom side such that the reflected signal part exits the top side of the railhead at a distance from said at least one central railhead part so that the reflected longitudinal sound signal is substantially not received by a detector;
transmitting at least one ultrasonic first main signal from the railhead top side to the railhead bottom side so that said at least one ultrasonic first main signal is reflected by the railhead bottom side towards a substantially central railhead part; and
transmitting at least one ultrasonic first verification signal from the railhead top side to reach the railhead bottom side via a substantially central railhead part, or vice versa;
wherein an extension of the railhead bottom side and an extension of the railhead top side, viewed in a direction away from the substantially central railhead part, include an angle which is approximately 20°.

36. A method for detecting flaws in a railhead of a rail according to claim 34, wherein the transmitting and receiving steps include:
    transmitting at least one ultrasonic longitudinal sound signal into the railhead via said railhead top side, such that at least a part of the longitudinal sound signal propagates through the railhead as a creep wave near the railhead top side, and
    detecting creep wave parts which have been reflected back from the railhead and exit the railhead top side;
    wherein at least two different ultrasonic longitudinal sound signals are transmitted into the railhead top side at different angles, so that
    at least one first ultrasonic longitudinal sound signal is transmitted into the railhead in a first rail longitudinal direction to form at least one respective creep wave, and
    at least one second ultrasonic longitudinal sound signal is transmitted into the railhead substantially in an opposite rail longitudinal direction to form at least one respective creep wave;
    using a plurality of said first ultrasonic longitudinal sound signals as positioning signals, to position at least a part of a measuring apparatus with respect to the railhead and/or
    determining the position of a center plane of the railhead;
    wherein said railhead bottom side is separated into a first bottom side part and a second bottom side part by a rail flange, and
    wherein a first transmitter transmits a first positioning signal into the railhead such that said first positioning signal is reflected via the first bottom side part of the railhead towards a first receiver, wherein the first positioning signal is received by the first receiver,
    and wherein a second transmitter transmits a second positioning signal into the railhead such that said second positioning signal is reflected via the second bottom side part of the railhead towards a second receiver, wherein the second positioning signal is received by the second receiver, and
    wherein transmission times of the first and second positioning signal are measured and are compared to one another to position the transmitters and receivers and/or a measuring apparatus with respect to the railhead.

37. A method for detecting flaws in a railhead of a rail according to claim 35, the method comprising:
    transmitting at least one ultrasonic longitudinal sound signal into the railhead via said railhead top side, such that at least a part of the ultrasonic longitudinal sound signal propagates through the railhead as a creep wave near the head top side;
    detecting at least some creep wave parts which have been reflected back from the railhead and exit the rail head top side;
    transmitting at least two different ultrasonic longitudinal sound signals into the railhead top side at different angles;
    transmitting at least one ultrasonic longitudinal sound signal into the railhead in a first rail longitudinal direction to form at least one respective creep wave;
    transmitting at least one other longitudinal sound signal into the railhead substantially in an opposite rail longitudinal direction to form at least one respective creep wave;
    using a plurality of said first signals as positioning signals, to position at least a part of a measuring apparatus with respect to the railhead and/or;
    using a plurality of said first signals to determine the position of a center plane of the railhead;
    wherein said railhead bottom side is separated into a first bottom side part and a second bottom side part by a rail flange, and a first transmitter transmits a first positioning signal into the railhead such that said first positioning signal is reflected via the first bottom side part of the railhead towards a first receiver, and wherein the first positioning signal is received by the first receiver, and wherein a second transmitter transmits a second positioning signal into the railhead such that said second positioning signal is reflected via the second bottom side part of the railhead towards a second receiver, and wherein the second positioning signal is received by the second receiver; and
    measuring and comparing transmission times of the first and second positioning signal to one another to position the transmitters and receivers and/or a measuring apparatus with respect to the railhead.

38. An apparatus for detecting flaws in a railhead, which apparatus is structured and arranged for carrying out a method according to claim 36.

39. An apparatus for detecting flaws in a railhead, which apparatus is structured and arranged for carrying out a method according to claim 37.

40. An assembly according to claim 20, wherein:
    each of said at least one first ultrasonic sound source and each of said at least one first detector are arranged relative to each other at a distance which is shorter than a width of the railhead;
    each first ultrasonic sound source is disposed in a transmitting position so that a respective transmitting direction is directed slightly away from the at least one central railhead part; and
    each first detector is disposed in a respective receiving position so that a respective receiving direction is directed towards the at least one central railhead part;
    wherein said railhead bottom side is separated into a first bottom side part and a second bottom side part by a rail flange,
    wherein the assembly includes a plurality of transmitters and receivers, respectively to transmit first and second positioning signals into the railhead and to receive reflected first positioning signals and reflected second positioning signals from the railhead,
    the first transmitter adapted to transmit a first positioning signal via the first railhead bottom side part to a first receiver, and
    the second transmitter adapted to transmit a second positioning signal via the second railhead bottom side part to a second receiver; and
    a processor to compare transmission times of the reflected first positioning signal and reflected second positioning signal,
    the processor further adapted to position at least a part of the detection apparatus with respect to the center of the railhead based on the comparison of the said transmission times;
    the railhead is provided with a top side and a bottom side, wherein the apparatus is movable over the top side of the railhead, in a particular direction of movement which is parallel to a rail longitudinal direction, wherein the apparatus is provided with at least one sound source which is at least designed to transmit ultrasonic longitudinal sound, wherein the apparatus is provided with at least one receiver which is at least designed to detect ultrasonic sound, wherein the longitudinal sound source and the detector can operatively be brought into such a respective transmitting position and receiving position that a respective transmitting direction and respective receiving direction each extend substantially transverse to a rail longitudinal direction, and are directed to a central railhead part;

said longitudinal sound source and the detector are each arranged along a virtual transverse plane of said direction of movement, wherein the longitudinal sound source and the detector are, in particular, operatively arranged next to or near each other, for instance at a distance which is shorter than a width of the railhead;

the railhead is provided with a top side, wherein the apparatus is movable over the top side of the railhead, in a particular direction of movement which is parallel to a rail longitudinal direction, wherein the apparatus is provided with at least one sound source which is arranged for transmitting at least one ultrasonic longitudinal sound signal into the railhead via said head top side, such that at least a part of the longitudinal sound signal propagates through the railhead as a creep wave near the head top side;

at least two sound sources are provided to transmit at least two different ultrasonic longitudinal sound signals into the railhead top side at different angles;

the apparatus is provided with at least one detector which is arranged for detecting ultrasonic signals, in particular at least creep wave parts, which have operatively been reflected in the railhead and exit the head top side;

the apparatus is provided with at least one sound source which is arranged for transmitting at least one said longitudinal sound signal into the railhead substantially in a first rail longitudinal direction for forming a respective creep wave, wherein the apparatus is provided with at least one other sound source which is arranged for transmitting at least one other longitudinal sound signal into the railhead substantially in an opposite rail longitudinal direction for forming a respective creep wave.

41. A control program that is disposed on a computer-readable medium, executable on a controller, and provided with program codes that make the controller at least suitable for carrying out the method according to claim 36, after the controller has been loaded with the control program for the purpose of controlling one or more sound sources and detectors.

42. A control program that is disposed on a computer-readable medium, executable on a controller, and provided with program codes that make the controller at least suitable for carrying out the method according to claim 37, after the controller has been loaded with the control program for the purpose of controlling one or more sound sources and detectors.

43. An apparatus for detecting flaws in a railhead of a rail, being an apparatus of an assembly according to claim 40.

44. Use of an apparatus according to claim 43 for testing rails for defects.

* * * * *

UNITED STATES PATENT AND TRADEMARK OFFICE
CERTIFICATE OF CORRECTION

| | | |
|---|---|---|
| PATENT NO. | : 8,020,446 B2 | Page 1 of 1 |
| APPLICATION NO. | : 11/884596 | |
| DATED | : September 20, 2011 | |
| INVENTOR(S) | : Pieter Bestebreurtje | |

It is certified that error appears in the above-identified patent and that said Letters Patent is hereby corrected as shown below:

In the Claims

Column 20, claim 35, line 51, "30'" should read --30°--.

Signed and Sealed this
Tenth Day of June, 2014

Michelle K. Lee
*Deputy Director of the United States Patent and Trademark Office*